United States Patent [19]

Turteltaub et al.

[11] Patent Number: 5,209,919
[45] Date of Patent: May 11, 1993

[54] METHOD OF MEASUREMENT IN BIOLOGICAL SYSTEMS

[75] Inventors: Kenneth W. Turteltaub, Livermore; John S. Vogel, Union City; James S. Felton, Danville; Barton L. Gledhill, Alamo; Jay C. Davis; Larry H. Stanker, both of Livermore, all of Calif.

[73] Assignee: Regents of the University of California, Oakland, Calif.

[21] Appl. No.: 693,248

[22] Filed: Apr. 26, 1991

Related U.S. Application Data

[63] Continuation-in-part of Ser. No. 553,080, Jul. 13, 1990, abandoned.

[51] Int. Cl.$^5$ .................. A61K 43/00; C01G 21/14; A61N 5/00
[52] U.S. Cl. ........................ 424/1.1; 435/56; 600/3; 128/154; 128/659
[58] Field of Search ............... 424/1.1; 436/56; 600/3; 128/654, 659

[56] References Cited

U.S. PATENT DOCUMENTS

| | | | |
|---|---|---|---|
| 3,649,199 | 3/1972 | Littlejohn | 23/230 |
| 4,022,876 | 5/1977 | Anbar | 424/1.1 |
| 4,037,100 | 7/1977 | Purser | 250/281 |
| 4,223,004 | 9/1980 | Hsia et al. | 424/9 |
| 4,224,031 | 9/1980 | Mee et al. | 23/230 |
| 4,454,233 | 6/1984 | Wang | 436/525 |
| 4,701,419 | 10/1987 | Morris | 436/89 |
| 5,045,479 | 9/1991 | Newman et al. | 436/518 |
| 5,078,135 | 1/1992 | Caprioli | 128/632 |
| 5,124,267 | 6/1992 | Humpel et al. | 436/518 |

OTHER PUBLICATIONS

D. Elmore, "Ultrasensitive Radioisotope, Stable-Isotope, and Trace-Element Analysis in the Biological Sciences Using Tandem Accelerator Mass Spectrometry," vol. 12, 1987.

J. Keilson et al., "Possible impact of the new spectrometric techniques on 14C tracer kinetic studies in medicine," University of Rochester, Apr. 1978.

A. Litherland, "Ultrasensitive Mass Spectrometry with Accelerators," vol. 30, pp. 437–473, 1980.

L. Brown, "Applications of Accelerator Mass Spectrometry," Ann Rev Earth Planet Sci, vol. 12, pp. 39–59, 1984.

(List continued on next page.)

*Primary Examiner*—Robert L. Stoll
*Assistant Examiner*—C. Sayala
*Attorney, Agent, or Firm*—Daryl S. Grzybicki; Henry P. Sartorio

[57] ABSTRACT

Disclosed is a method of quantifying molecules in biological substances, comprising:
a. selecting a biological host in which radioisotopes are present in concentrations equal to or less than those in the ambient biosphere,
b. preparing a long-lived radioisotope labeled reactive chemical specie,
c. administering said chemical specie to said biological host in doses sufficiently low to avoid significant overt damage to the biological system thereof,
d. allowing a period of time to elapse sufficient for dissemination and interaction of said chemical specie with said host throughout said biological system of said host,
e. isolating a reacted fraction of the biological substance from said host in a manner sufficient to avoid contamination of said substance from extraneous sources,
f. converting said fraction of biological substance by suitable means to a material which efficiently produces charged ions in at least one of several possible ion sources without introduction of significant isotopic fractionation, and,
g. measuring the radioisotope concentration in said material by means of direct isotopic counting.

29 Claims, 4 Drawing Sheets

OTHER PUBLICATIONS

A. Litherland, "Accelerator Mass Spectrometry," Nucl. Inst. & Meth. in Phy. Rsch B5, pp. 100–106, 1984.

J. Vogel, et al., "Application of Accelerator Mass Spectrometry to Biomedical Sciences," Battelle Conference Center, Seattle, Wash., Apr. 4–5, 1990.

K. Turteltaub et al., "Accelerator Mass Spectrometry in Biomedical and Environmental Sciences," LLNl, Apr. 10, 1990.

K. Turteltaub et al., "Accelerator Mass Spectrometry in Biomedical Dosimetry: Relationship between Low–Level Exposure and Covalent Binding of Heterocyclic Amine-carcinogens to DNA," LLNL, Apr. 13, 1990.

J. Vogel et al., "Application of AMS to the Biomedical Sciences," LLNl, Apr. 18, 1990.

J. Felton et al., "Accelerator Mass Spectrometry in the Biomedical Sciences: Applications in Low-Exposure Biomedical and Environmental Dosimetry," LLNL May 10, 1990.

Pub. Release from LLNL, "Livermore Scientists Develop New Cancer Research Tool," Thursday, May 24, 1990.

J. Vogel et al., "Memory Effects in an AMS System: Catastrophe and Recovery," Radiocarbon, vol. 32, No. 1, pp. 81–83, 1990.

Multi–desciplinary Tandem Accelerator Laboratory, LLNL E&TR, Jun. 1987, pp. 14–20.

METHOD OF MEASUREMENT IN BIOLOGICAL SYSTEMS

The U.S. Government has rights in this invention pursuant to Contract No. -7405-ENG-48 between the U.S. Department of Energy and the University of California for the operation of Lawrence Livermore National Laboratory.

This application is a continuation-in-part of application Ser. No. 07/553,080, filed Jul. 13, 1990 now abandoned which is incorporated herein by reference.

BACKGROUND OF THE INVENTION

1. Field of the Invention

The present invention relates to a method of measurement in biological systems. More particularly, it relates to a method of quantifying molecular mixtures of and adhesions to minute amounts of biological substances using an accelerator mass spectrometer. Still more particularly, it relates to a process of measurement using intermediate and long lived isotopes bound to biological substances which are then converted to forms suitable for analysis by accelerator mass spectrometry.

Isotopes of various elements, particularly $^{14}C$, have been used in biological processes for some time as a means of tracing, to determine fate and speeds of reaction processes, and for other purposes.

The measurements are made by scintillation counters, autoradiography or other devices which measure the amount of decay of isotopes which have a relatively short half life.

These methods, in general, cannot be used where human beings are involved because of the potential radiation damage from the isotopes and the amount of sample required. At radiation levels which are not harmful to humans, decay counting methods are insufficiently specific and sensitive to give meaningful results. Moreover, the background contamination is high, creating problems for the users of the equipment.

2. The Prior Art

Isotopes are also used in biological systems for specific assays. The prior art of competition radio-immune assays (RIA) depends on the quantification of the number of radioactively labeled molecules which bind to their specific antibody in competition with an unknown amount of unlabeled molecules of the same chemical or class of chemicals. The number of labeled molecules binding to the antibodies is compared to the number of such molecules which bind to the antibody if no competitor molecules are present. This ratio of the bound, labeled molecules to the maximum possible number of bound molecules is then compared to a calibration curve to determine the number of unknown molecules which compete with the labeled molecules for binding locations on the antibody. This calibration curve is derived from similar measurements wherein known amounts of unlabeled molecules have been added to the solution of antibodies and labeled molecules.

These measurements depend on efficient separation of the antibodies and their bound molecules from the solution still containing labeled molecules. In the prior art, these antibodies are separated, for example, by immobilizing them on the walls or bottom of a tube or cell in which a known amount of the labeled chemical is added along with the unknown amount of chemical to be assayed. After the reactions of the molecules with the immobilized antibodies, the unbound reactants are separated from the antibodies by removal of the solution, followed by several rinses of the inside of the tube or well containing the immobilized antibodies. The tube or well is filled with or placed in a liquid scintillant and the radioisotope content is found using a scintillation counter. The sensitivity of a radio-immune assay is a function of the concentration of antibodies and radiolabeled molecules which are used. More sensitivity is gained by using lower concentrations of these reactants. These concentrations cannot be decreased substantially in the prior art of radio-immune assays, because the scintillation counters used to quantify the binding to the antibodies detect not only the bound radioisotopes but also spurious charged particles from cosmic rays or radioactive contaminations within the counter as well as the radio-labeled molecules which have bound directly to the surfaces of the tube or well without an intermediary antibody. These 'background' events are indistinguishable from the particles which result from the decay of the radioisotopes in the molecules bound to the antibodies.

One way to increase sensitivity in an RIA is to use labelling isotopes which have short half-lives or decay times, such as isotopes of iodine. For a given amount of bound molecules, more counts will be detected above the counter background when shorter-lived isotopes are used. However, the concentration of these short-lived isotopes changes rapidly in time, so that chemical compounds incorporating these isotopes are used quickly after production. Calibration curves must be corrected often to account for this rapid decrease in the radioactivity of the labeled compounds. Further, these short-lived isotopes are often linked to the molecule in labile positions which allows them to deattach from the chemical compound of interest and cause another uncertainty in the quantification of the number of labeled molecules bound to antibodies.

A suggested solution of overcoming the problems associated with the use of short half life isotopes is to use an accelerator mass spectrometer.

As described by D. Elmore in an article in Biological Trace Element Research, Vol. 12, 1987, accelerator mass spectrometers can be used for a variety of purposes using long-lived radioisotopes. Such purposes include the introduction of isotopes as a tracer, then chemically processing the bulk tissue samples.

U.S. Pat. No. 4,037,100 describes an apparatus which can be used for the detection of electronegative particles and provide data as to their elemental composition. The apparatus includes an accelerator mass spectrometer (AMS) which can be used for making mass and elemental analyses. Still other references to AMS devices, and their uses include: Kilius et. al, "Separation of $^{26}AL$ and $^{26}Mg$ Isobars by Negative Ion Mass Spectrometry," Nature, Vol. 282, November 1979; A. E. Litherland, "Acceleration Mass Spectrometry," Nuclear Instruments and Methods in Physics Research B5, pp. 100–108, (1984); L. Brown, "Applications of Accelerator Mass Spectrometry," Ann. Rev. Earth Planet. Sci., Vol. 12, pp. 39–59, (1984); and A. E. Litherland, "Ultrasensitive Mass Spectrometry with Accelerators," Ann. Rev. Nucl. Part. Sci., Vol. 30, pp. 437–473, (1980).

Accelerator mass spectrometry (AMS) was developed as a highly sensitive method for counting long-lived but rare cosmogenic isotopes, typically those having half-lives between $10^3$ and $2 \times 10^7$ years. Isotopes with this range of half-lives are too long-lived to detect easily by conventional decay counting techniques but are too short-lived on geological timescales to be present in appreciable concentrations in the biosphere or lithosphere. Assay of these cosmogenic isotopes ($^{10}Be$, $^{14}C$, $^{26}Al$, $^{41}Ca$, $^{36}Cl$, and $^{129}I$) by AMS has become a fundamental tool in archaeology, oceanography, and the geosciences, but has not been applied to problems of a biological or clinical nature.

It is an object of this invention to provide a method of biological analyses which is more specific than prior art methods.

It is a further object of this invention to provide a method of quantitive biological analysis which is more sensitive than methods known heretofore.

It is a still further object of this invention to provide a method of quantifying molecular mixtures of and adhesions to minute amounts of biological substances.

It is yet another object of this invention to provide a method of quantitive biological analysis using rare stable isotopes.

Another object of the invention is to provide a technique to measure the concentrations of long-lived radioisotopes at levels of a few parts in $10^{15}$ to parts in $10^8$ which can signal the presence or effects of very small amounts of labeled exogenous biochemicals within biological systems, organs, fluids, cells or parts of cells of living hosts, including humans.

Another object of the invention is to provide a technique to measure the concentrations of long-lived radioisotopes from within biological systems which does not make use of the radioactive decay of these isotopes.

Another object of the invention is to provide a technique to quantify the amount of an exogenous biochemical or several parts of an exogenous biochemical which have become adhered to or mixed with the natural biochemicals of a biological system using long-lived, radioactive molecular labels which are too low in concentration to be detected using techniques which depend on the decay of the radioisotopes.

Another object of the invention is to provide a technique to measure the concentrations of long-lived radioisotopes from within biological systems in which the labeled exogenous biochemical is stable over periods of time which are long compared to the period of biological effectiveness.

Another object of the invention is to provide a technique to measure the concentrations of long-lived radioisotopes from within biological systems in which the labeled exogenous biochemical is a close analogue of the natural, unlabeled form of the biochemical and without resort to the substitution of elements within the biochemical by short-lived radioisotopes of other similar elements or chemically labile short-lived radioisotopes.

Still another object of the invention is to provide a technique to measure the concentration of long-lived radioisotopes from within biological systems which represent molecular events whose probability is so low that natural levels of radioisotopes would mask the radioisotope labels attached to the exogenous effector.

These and other objects of the invention will be realized in the description, drawings, and claims to follow.

SUMMARY OF THE INVENTION

The present invention is a method of measurement in biological systems, i.e., a method of quantifying mixtures and adhesions to very small amounts of biological substances utilizing an accelerator mass spectrometer. As used herein the term "biological substance" refers to plant, animal, and marine substances, i.e., all living matter.

The method of the invention comprises the following steps:

a. selecting a biological host in which radioisotopes are present in concentrations equal to or less than those in the ambient biosphere, b. preparing a long-lived radioisotope labeled reactive chemical specie, c. administering said chemical specie to said biological host in doses sufficiently low to avoid significant overt damage to the biological system thereof, d. allowing a period of time to elapse sufficient for dissemination and interaction of said chemical specie with said host throughout said biological system of said host, e. isolating a reacted fraction of the biological substance from said host in a manner sufficient to avoid contamination of said substance from extraneous sources, f. converting said fraction of biological substance by suitable means to a material which efficiently produces charged ions in at least one of several possible ion sources without introduction of significant isotopic fractionation, and, g. measuring the radioisotope concentration in said material by means of direct isotopic counting.

DETAILED DESCRIPTION OF THE INVENTION

Figure 5:
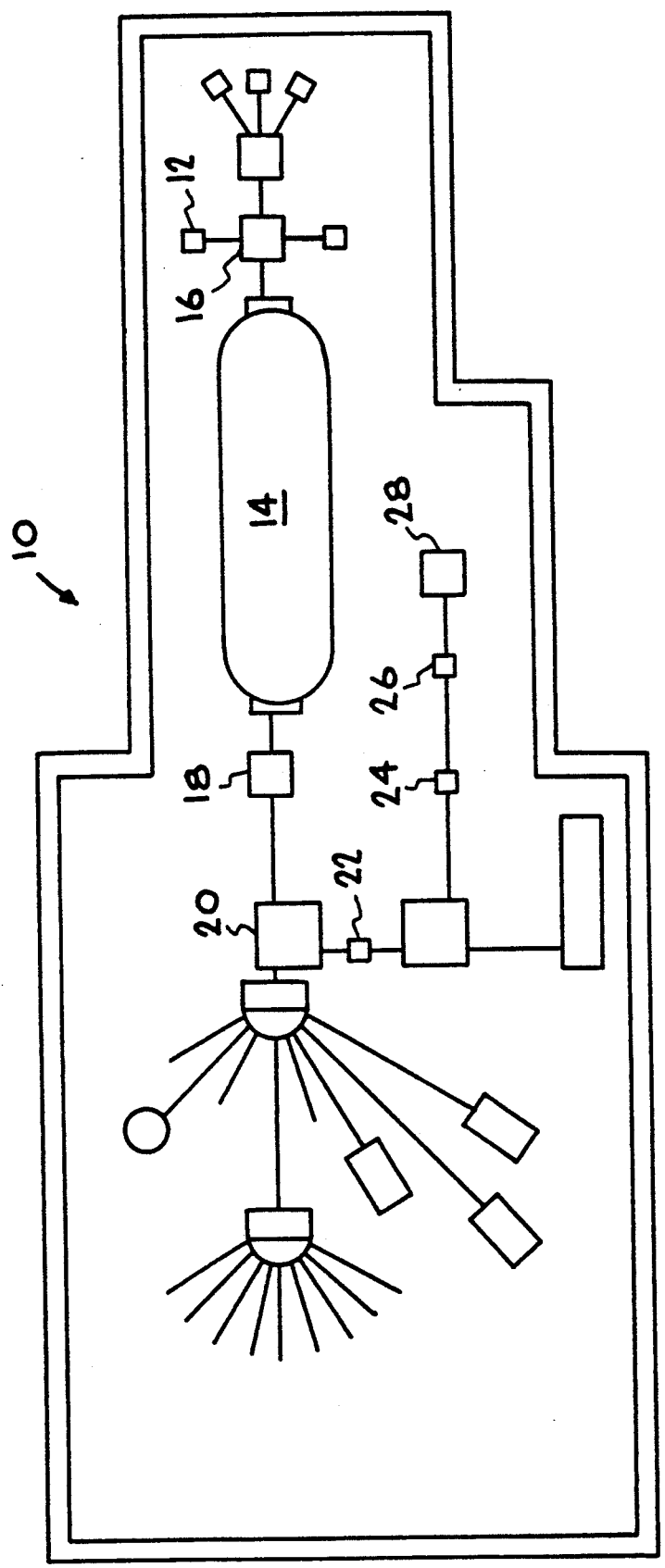
FIG. 5. Is a schematic drawing of apparatus used in carrying out the method of the invention.

The method of the invention is carried out with the use of an accelerator mass spectrometer (AMS). Such devices can be purchased on the open market, but the specific one used to carry out the procedures described in the examples below was custom built at Lawrence Livermore National Laboratory. It is shown in FIG. 5 and is described as follows:

Beam Optics Design

The spectrometer 10 was designed using the beam optics code OPTRYK. An important design aim was to achieve high sample throughput through use of a high intensity multi-sample ion source. Operation at high current raised the possibility of intensity-dependent beam losses in the system arising from space charge effects near the source. The system was therefore designed for the best possible beam transmission to minimize such effects. Other important considerations included ease of tuning and operation through provision of adequate beam diagnostics and corrective steerers, and computer control of the transport system to allow eventual unattended operation.

Ion Source and Injection

The present AMS ion source 12 is a Genus Model 846 sputter source, equipped with a 60-sample charger. Operating voltages are 8 kV on the source cathode plus 25-30 kV on the extraction, for a total injection energy of just 35 kV. The decision was taken not to place the source on a high voltage deck, since the large calculated acceptance of the modified FN 14 indicated that beam transmission for typical sputter source emittances would be excellent, and the design of the injection beam line is simplified. Beams from the source are focussed by an einzel lens on to the object slits of a 90° double-focussing Danfysik injection magnet 16 ($r=50$ cm, $ME/Z^2=7.5$). The magnet is provided with rotatable downstream pole tips so that a second ion source leg opposite the present one can be implemented. The vacuum box is insulated to +5 kV. By means of high voltage switches connecting the box to DC power supplies or to ground, different isotopes are switched into the accelerator under control of the data acquisition system. A large magnet gap of 5 cm was specified to ensure good transmission, and the accel-deccel gaps placed near the magnet object and image positions were also made large (10 cm diameter) to increase the lens focal lengths and thus minimize differential focussing for different bias voltages.

Accelerator

The FN accelerator 14 was obtained from the University of Washington, Seattle, and has been substantially upgraded. Dowlish, titanium spiral-inclined-field accelerator tubes and a Pelletron conversion were installed to increase the beam transmission and the terminal voltage range, and to improve energy stability and reliability. Although the entrance grid of the #1 Dowlish tube intercepts 10% of the injected beam, this loss is insensitive to changes in the beam size or position and so can be tolerated. The beam transmission with these tubes is otherwise excellent. Other improvements to the FN 14 included installation of a large (1 cm) diameter stripper canal and a turbomolecular terminal pump, for increased transmission with gas or foil strippers. Systems in the terminal are presently controlled via plastic rods, but an infrared light link control system can be used. The terminal voltage stabilization system currently relies on generating voltmeter and capacitive pickoff inputs, and voltage stabilities of about 1 part in $10^4$ are achieved. A slit stabilization system is under construction.

The accelerator operating voltages were limited to 5.5 MV by the use of $N_2/CO_2$ insulating gas until the gas handling system had been thoroughly exercised and made leak-tight. The gas has been replaced with $SF_6$ and the FN has been conditioned to 9.0 MV. The FN now operates uneventfully at 7 MV, so that optimum running conditions for the $C^{4+}$ charge state are attainable, and it is anticipated that further voltage increases to 10-11 MV will be routine.

High Energy Spectrometer

Scattering in the stripper in the accelerator terminal inevitably increases the emittance of the transmitted beam sufficiently to cause some losses in the high energy accelerator tubes, particularly for heavy isotopes and low energies. The high energy spectrometer was designed to pass the maximum beam divergence that could emerge from the Dowlish tubes to the AMS detectors without loss. This proved unexpectedly easy to accomplish using surplus large quadruples and analyzing magnets from LLNL and from the HEPL laboratory at Stanford University. A design consisting of two identical 90° magnets and a Wien filter was chosen for its good optical properties and compact layout.

Beams from the FN are focussed by a 10 cm diameter magnetic quadruple triplet 18 to the object point for the first analyzing magnet 20. The choice of magnetic quadruples is a compromise, since correct focussing is achieved for just one isotope at a time. The triplet misfocussing is accommodated by opening the object slits and was taken into account in the positioning of the Faraday Cups 22 which detect analyzed stable isotope beams. Since the analysis magnet gap is large, beam losses are avoided.

The two identical ex-HEPL dipoles (single-focussing, $r=139$ cm, gap$=6.4$ cm, $ME/Z^2=150$) together form a first-order achromat, leading to a small beam waist at the start of the final beam line leg and reducing any jitter from energy shifts. The momentum dispersion at the image slits of the first magnet is about 1 in 800. Stable beams are detected in Faraday Cups 22 in a large vacuum chamber downstream of the magnet, and these cups are equipped with internal slits for beam position monitoring and for terminal voltage stabilization. The pole width is sufficiently wide that masses 12-14 could be accommodated without changing the magnet field, but this would require a new vacuum tank, and only $^{13}C$ and $^{14}C$ are accelerated at present.

The final beam line leg contains a second magnetic triplet 24, a Wien filter 26, and the AMS detectors 28. The Wien filter (length$=1$ m, gap$=8$ cm, 3 kG, 60 kV) was built by Danfysik and is a scaled up version of one used previously by the Simon Fraser AMS group, with a velocity resolution $\sim\Delta v/v$ for 22.5 MeV $C^{4+}$ of about 1/120. The filter was preferred over electrostatic deflectors for the versatility provided by its variable dispersion and for the ease of alignment arising from the straight-line beam path. The optical magnification of the final leg was deliberately made large to provide a small final beam divergence. Longitudinal detector positions are less critical and time-of flight detectors of modest length can be implemented without using refocussing quadruples. Ample space is available to extend the line if long flight paths and refocussing prove necessary.

Data Acquisition

Particle detection is by means of a multi-anode transverse gas ionization detector. A longitudinal gas ionization detector for Be and two carbon foil channel plate time-of-flight detectors for heavy isotopes are currently under construction. Data acquisition is based on NIM and CAMAC electronics feeding CAMAC ADC's and scalers, with HP9000 workstations running under UNIX and in-house acquisition software written in C.

Control System

The accelerator and beam line elements are computer-controlled through CAMAC and HP9000 workstations, using a control system developed at LLNL and the CEBAF laboratory. Local computers each communicate via GPIB with a single CAMAC crate which controls a cluster of beam line elements. A supervisory computer at the operator console scans the local computers via a LAN, with a systemwide data update rate of about 10 Hz. The supervisor also controls the main graphics display, flags errors, and receives operator input through the keyboard or via 9 reassignable knobs. All definitions of signal connections and control algorithms are set up by manipulating icons with a graphics editor, so that control functions can be changed without writing new code.

The system controls the entire spectrometer, with the exceptions of the source sample changer, and the injection bounce timing which is driven by the data acquisition system.

Biomedical Applications

Carcinogens covalently bound to any of the deoxynucleotide bases present in DNA (DNA adducts) have been touted as markers of carcinogen exposure. The relationship between adduct formation and exposure, however, has been primarily established at high carcinogen doses and not at lower, more environmentally relevant levels, due to limitations in assay sensitivity. As a consequence, the significance of using adducts as a measure of carcinogen exposure in the human population is unknown. Currently, the most sensitive technique for adduct detection is the $^{32}$P-postlabeling assay. The $^{32}$P-postlabeling assay has permitted measurement of 1 adduct in $10^{10}$ nucleotides and has been used to detect carcinogen-DNA binding in occupationally-exposed humans and smokers, but accurate quantitative measurement at levels less than 1 adduct/$10^7$–$10^8$ nucleotides is difficult due to variability in adduct recovery.

The great enhancement in $^{14}$C detection sensitivity available with AMS offers the distinct advantage of detecting extremely small amounts of covalently bound $^{14}$C-labeled carcinogens to DNA with known stoichiometry over a wide range of carcinogen binding.

Historically, measurement of isotopically-tagged materials has been avoided by AMS laboratories due, at least in part, to concerns over facility contamination. Initial measurements on biological materials have shown that contamination of AMS instrumentation by samples prepared in biomedical laboratories with a history of $^{14}$C usage is indeed a problem. In an effort to make this technology available to the biomedical and environmental sciences communities, new sample handling protocols have been devised to overcome such gross contamination.

Figure 1:
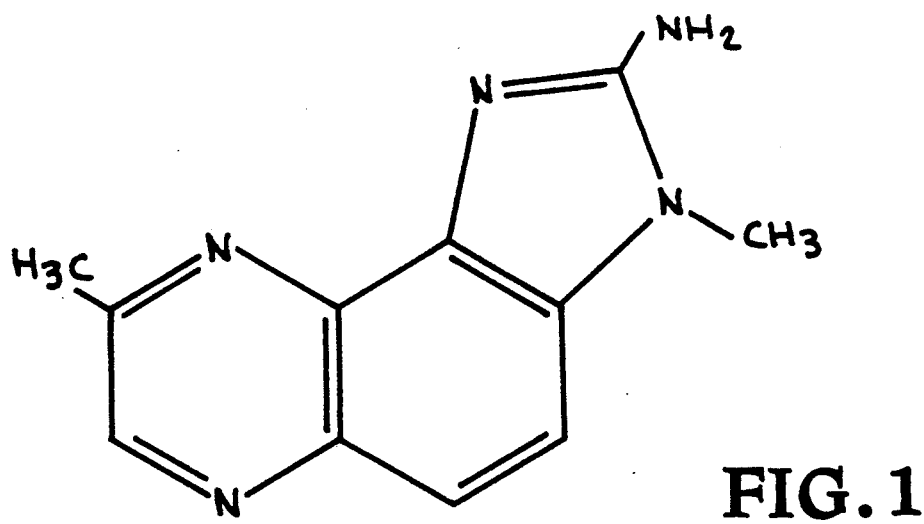
FIG. 1. Shows the structure of 2-amino-3,8-dimethlimidazo[4,5-f]quin-oxaline (MeIQx).

In the method of this invention these new protocols have been used to determine the relationship between carcinogen dose and DNA adduct levels in mice given very low levels of 2-amino-3,8-dimethylimidazo[4,5-f] quinoxaline (MeIQx; FIG. 1), a carcinogen found in cooked meat. This study provides the first report of the dynamic range, sensitivity and general applicability of AMS technology to problems in biomedical and environmental dosimetry, as well as presenting the relationship between DNA adducts and low-dose MeIQx exposure.

The method of the invention also presents an alternative way to increase the sensitivity of RIA by decreasing the amount of antibody and labeled compound using an accelerator mass spectrometer as the detector instead of a scintillation counter. Accelerator mass spectrometry has an efficiency for detecting rare isotopes which is not a function of the decay time or half-life of the isotope. Thus, the radio-isotope label in a compound is a longer-lived isotope, such as $^3$H, $^{14}$C or $^{79}$Se. Since the number of radio-isotopes in a sample is much greater (by orders of a million or billion than those that decay in any reasonable time), a direct detection of the isotopes using AMS permits a decrease in the amounts of reactants by a similar factor to obtain similar precision to that obtained by scintillation counting.

This invention will be more fully understood by reference to the following examples, which are intended to be illustrative of the invention, but not limiting thereof.

EXAMPLE 1

Measurement of recovered antigens and antibodies in a radio-immunoassay

The concentration of recovered antibodies and the concentration of recovered bound antigens are determined for a single sample from a radio-immunoassay by measuring the concentrations of both $^{14}$C which is used to label the antigen and the $^3$H which is used to label the binding antibodies in the same sample. Uniformly labeled 2,3,7,8-tetra-dibenzo-p-dioxin (TCDD) is obtained commercially containing an average of 11.7 $^{14}$C atoms per molecule of TCDD. Antibodies specific to the binding of TCDD are produced by monoclonal techniques. An essential amino acid, such as cystine, is provided to the cloning process in a commercially-available, radioactively-labeled form, such as [$^3$H]Cys. Alternatively, the sulfur atom in the cystine could be substituted by $^{79}$Se. The monoclonal antibodies are produced so that the labeled cystine is the sole source of cystine, which is required to make effective antibodies. For a specified immunoglobin, there is a specified amount of cystine and a concomittant specified amount of radioactive label in the antibody. In the usual manner of radio-immunoassays, the relation between the known concentration of labeled antigen and the fraction of that concentration which is bound to the antibodies for a fixed concentration of antibodies is found for a range of antigen concentrations which includes the expected antigen concentration to be assayed. The amount of the antigen bound to the antibody is usually found by radiometric determinations of the antigen's radioisotope label after the unbound fraction of the antigen has been separated from the bound antibody/antigens. The sensitivity of the usual immunoassay is limited by the requirement that sufficient radioactivity be present in the bound fraction for radiometric counting after whatever process is used to separate the unbound fraction of antigen. In this example, we measure the radioisotope concentration, and hence the bound antigen concentration, in the separated portions at sensitivities of $10^4$–$10^8$ molecules per micro-titer well by AMS techniques. The separation of bound antigen/antibody pairs from the solution containing unbound antigen or antibodies may be effected several ways and only one method is given here by way of example. The antibodies are fixed to very small glass beads, produced commercially for this purpose, and allowed to react with 100 μl solutions of the antigen in wells of micro-titer plates. After suitable incubation, the unbound fractions of labeled antigen are removed with the remaining solute, the beads holding the antibodies and the bound antigen are recovered and further separated from unbound antigen by simple rinsing, perhaps after application of a fixing agent to aid in the antigen binding as the chemical conditions change during processing. The beads holding the separated bound antigen are vacuum dried and combusted in flowing oxygen or in sealed contact with solid oxidants such as cupric oxide at 700° C. The resultant $CO_2$ is collected and graphitized through catalytic reduction by hydrogen over cobalt or iron powder at 600° C. The resultant graphite is pressed into sample holders for a fast-ion-bombardment ion source and the resultant ions are measured against standard $^{14}C$-containing materials in an accelerator mass spectrometer. For correct interpretation of the ratio of $^{14}C$ to the total carbon in a sample, the amount of antibody present in the separated sample is accurately determined from the weight of the glass beads, or other such measure. Any uncertainty in the concentration of the antibodies which are recovered through separation and purification processes introduces uncertainty in the standard '% Bound' versus 'Antigen Concentration' curve. Alternatively, this uncertainty is eliminated by measuring the amount of antibody which is involved in the binding of the measured bound antigen by use of the second radioisotope label which has been incorporated into the antibodies during production. In our example, the water produced from the combustion of the beads holding the antibody and antigen is collected separately from the $CO_2$. The water contains the $^3H$ which reflects the total amount of antibodies, bound and unbound, which are on the sampled glass beads. The water is reduced against powdered Zn at 350°-400° C. in a closed volume and the resultant $H_2$ is absorbed into titanium powder at 480°-650° C. The resultant titanium hydride is pressed into the sample holders of a fast-ion-bombardment ion source and the resultant hydrogen ions are analyzed using accelerator mass spectrometry. The samples which are to be immunoassayed are then prepared and measured in the same manner as the samples used in making the response curve for the known antigen/antibody binding concentrations. Alternatively to the individual preparation and measurement of the carbon and the hydrogen radioisotopes, the samples are reacted with strong Lewis acids, such as but not limited to aluminum bromide, which produces a material which can be used in the ion source and which contains both the carbon to be analyzed as well as the hydrogen to be analyzed. In this latter instance, the $^3H$ and the $^{14}C$ content are measured from the same sample during the same measurement, either by analyzing for the two isotopes simultaneously or alternately.

EXAMPLE 2

Preparation of organic biomedical samples for AMS determination of radio-isotope content Samples of organic biochemicals, such as albumin, cellulose, sucrose, collagen, whole skin, sodium dodecyl sulfate and other ionic detergents, have been made into a thermally conductive and chemically inert uniform substance for use in a fast-atom-bombardment ion source by interaction with molten Lewis acid salts. Milligram sized samples were placed in 6×50 mm borosilicate glass culture tubes. Liquid solutions of proteins and/or ionic detergents were pipetted into the tubes and the materials were vacuum dried. Solid samples such as collagen, skin or sucrose were placed directly into the tubes. Five to fifty milligram aliquots of the strong Lewis acid, anhydrous aluminum bromide, were added to the individual tubes. The tubes were placed within confinement vessels consisting of a 10×70 mm culture tube slipped within a 12×70 mm culture tube. The vessels containing the mixture of biochemical and aluminum bromide were then heated to over 100° C. but to no less than 150° C. for 1 to 5 hours. The vessels and the reactants were heated in vacuum, air, or argon atmospheres. The Lewis acid transformed the biochemicals to a black, inert, uniform substance. After the reaction had finished, excess Lewis acid was driven out of the sample by heating to beyond the boiling point of the acid. In this example, the samples were heated to 300°-400° C., well above the 263.3° C. boiling point of aluminum bromide. The Lewis acid condensed on the cooler vessel surfaces above the sample. The 6×50 mm culture tubes containing the modified samples were removed from the vessels and hydrated aluminum bromide, which remained within the sample material, was removed by repeated rinsing with water. The sample material was vacuum dried to remove adsorbed gas. In order to increase the thermal conductivity of the material, metal powders were added to the samples either before the interaction with the Lewis acid, or after the vacuum drying of the prepared material. Metals tested for this purpose included, but are not restricted to, silver, titanium, cobalt. The use of titanium during the reaction with a strong Lewis acid promoted the inclusion of the hydrogen in the sample within the finished material. The finished material was pressed into sample holders which were placed in the cesium sputter source of the LLNL AMS facility. In order to reduce the thermal deposition into the sample, the ion source was operated at a relatively low cathode potential of 2.5–4 kV relative to the extraction potential. Negative carbon atomic ion currents equal to 25 to 45% of those available from prepared filamentous graphite were extracted from the ion source. These ion beams were analyzed using normal AMS techniques.

EXAMPLE 3

Detection of Amino-imidazoazaarene Adducts on DNA

The covalent binding of 2-amino-3,8-dimethylimidazo (4,5-F) quinoxaline (MeIQx), a carcinogen resulting from the cooking of meat, to murine hepatic deoxyribonucleic acids (DNA) was measured to a sensitivity of one DNA adduct per $10^{12}$ nucleotides. Eighteen (18) male C57BL/6 mice weighing 23–27 g were housed individually in new disposable polystyrene cages with hardwood bedding on a 12 hr light/dark cycle. Animals were fasted for 18 hr and then given single doses of [2-$^{14}C$]-MeIQx (50 mCi/mMol) which was synthesized (1) in our laboratory. New disposable syringes, gavage needles, and gloves worn by the technician were used for administration of the MeIQx to each animal. Each of the five dose levels were replicated 3 times. The radiopurity of the compound was greater than 97% as determined by high pressure liquid chromatography. Administration of the [$^{14}C$]-MeIQx was in corn oil by stomach intubation (0.1 ml volume). Doses of MeIQx were administered from 500 pg/kg to 5 mg/kg body weight. An additional set of 3 animals given only corn oil were used as controls. Animals were housed in ventilated negative air flow isolation units previously determined to be $^{14}C$-free by AMS and were sacrificed 24 hr after dosing by $CO_2$ asphyxiation. Each animal was sacrificed and handled separately beginning with control animals in the order of increasing MeIQx dose. New dissection scissors and forceps were used on each animal and gloves were changed often to avoid cross-contamination of the tissues. Each dissection was carried out on freshly laid paper-covered laboratory benches and the paper covering was changed between each animal dissection. Livers were placed in individual disposable 50 ml centrifuge tubes, frozen on dry ice immediately following removal, taken to a separate laboratory, and the DNA was isolated as previously described (2) using freshly prepared solutions. Following DNA isolation, the DNA was dissolved in distilled water, extracted 3 times with aqueous 1-butanol, pH 8.0, and dialysed against sterile distilled water 3 times to insure removal of any residual noncovalently bound $^{14}C$. Samples were handled using disposable glassware in the order of increasing MeIQx dose. All equipment was used only once. Gloves were worn throughout the procedures and were changed between each sample. The DNA was then diluted from 10 to 1,000-fold with a 1 mg/ml sodium lauryl sulfate (SDS) solution which was previously determined to be 0.47 parts $^{14}C$ in $10^{12}$. Approximately 0.5 mg of the DNA/SDS mixture was dried under vacuum in silica tubes, was combusted to $CO_2$ in sealed, evacuated tubes with CuO at 900° C. and reduced to filamentous graphite by hydrogen over a cobalt catalyst using a dedicated system built for handling labeled compounds as described by Vogel et al. (3,4). $^{14}C$ free acrylamide and ANU sucrose standards (prepared by the Australian National University) were graphitized along with the samples to monitor for $^{14}C$ carry-over. Water vapor degassing between preparations helped to remove residual $^{14}C$ remaining in the instrumentation. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (5,6). ANU sucrose, with an activity 1.508 times the $^{14}C$ activity of 1950 carbon, was used as analytical standard. Measurements are reported in units of Modern or as DNA adducts/$10^{12}$ nucleotides. Modern is defined as $5.9 \times 10^{10}$ 14C atoms/g carbon and is approximately equal to the natural abundance of $^{14}C$ present in contemporary (1950 A.D.) carbon (7). Determination of adduct levels is based on $^{14}C$ measurement of the MeIQx DNA adduct. [$^{14}C$]-MeIQx binding was calculated by subtraction of the natural radiocarbon content from the measured $^{14}C$ content of the samples. Adduct frequencies were normalized based on the assumption that 1 μg DNA = 3240 pMol nucleotides. The lowest level of MeIQx DNA binding was detected at 1 adduct per $10^{11}$ deoxyribo-nucleotides and the number of 1 adducts per $10^{12}$ deoxynucleotides was linear with dose.

References

1. Grivas, S. (1985) *Acta Chem. Scand. Ser. B.* 39, 213-217.
2. Gupta, R. C. (1984) *Proc. Natl. Acad. Sci.*, USA 81, 6943-6947.
3. Vogel, J. S., Nelson, D. E., and Southon, J. R. (1989) *Radiocarbon* 31, 145-149.
4. Vogel, J. S., Nelson, D. E., and Southon, J. R. (1987) *Radiocarbon* 29, 323-333.
5. Davis, J. C. (1989) *Nucl. Instrum. Methods* B40/41, 705-708.
6. Proctor, I. D. (1989) *Nucl. Instrum. Methods.* B40/41, 727-730.
7. Stuiver, M., and Polach, H. A. (1977) *Radiocarbon* 19, 355-363.

EXAMPLE 4

Demonstration that 2,3,7,8-tetrachlorodibenzo-p-dioxin does not covalently bind to DNA 2,3,7,8-tetrachloro-[U-$^{14}C$]dibenzo-p-dioxin (TCDD) was tested for its ability to covalently bind to murine hepatic deoxyribonucleic acids and thus for its potential to initiate mutagenesis at exposure concentrations well below the maximum tolerated dose and the lethal dose in this species. [U-$^{14}C$] TCDD, 122 mCi/mMol, >97% radiopurity by high pressure liquid chromatography, was purchased from Cambridge Isotope Laboratories (Woburn, Mass.). The TCDD was diluted in p-dioxane for administration to the mice. Eighteen (18) male C57BL/6 mice weighing 23-27 g were housed individually in new disposable polystyrene cages with hardwood bedding on a 12 hr light/dark cycle. Animals were fed ad Libitum. [U-$^{14}C$]TCDD was administered by intraperitonal injection (10 μl total volume). New disposable syringes, needles, and gloves worn by the technician were used for administration of the TCDD to each animal. Each of the five dose levels were replicated 3 times. Doses of TCDD were administered from 5 pg/kg to 100 pg/kg body weight. An additional set of 3 animals given only p-dioxane were used as controls. Animals were housed in ventilated negative air flow isolation units previously determined to be $^{14}C$-free by AMS and were sacrificed 24 hr after dosing by $CO_2$ asphyxiation. Each animal was sacrificed and handled separately beginning with control animals in the order of increasing TCDD dose. New dissection scissors and forceps were used on each animal and gloves were changed frequently to avoid crosscontamination of the tissues. Each dissection was carried out on freshly laid paper-covered laboratory benches and the paper covering was changed between each animal dissection. Livers were placed in individual disposable 50 ml centrifuge tubes, frozen on dry ice immediately following removal, taken to a separate laboratory, and the DNA isolated as previously described (1) using freshly prepared solutions. Following DNA isolation, the DNA was dissolved in distilled water, extracted 3 times with aqueous 1-butanol, pH 8.0, and dialysed against sterile distilled water 3 times to insure removal of any residual noncovalently bound $^{14}C$. Samples were handled using disposable glassware in the order of increasing TCDD dose. All equipment was used only once. Gloves were worn throughout the procedures and were changed between each sample. The DNA was then diluted from 10 to 1,000-fold with a 1 mg/ml sodium lauryl sulfate (SDS) solution which was previously determined to be 0.47 parts $^{14}C$ in $10^{12}$ total carbon. Approximately 0.5 mg of the DNA/SDS mixture was dried under vacuum in silica tubes, was combusted to $CO_2$ in sealed, evacuated tubes with CuO at 700° C. and reduced to filamentous graphite by hydrogen over a cobalt catalyst using a dedicated system built for handling labeled compounds as described by Vogel et al. (2,3). $^{14}C$-free acrylamide and ANU sucrose standards (prepared by the Australian National University) were graphitized along with the samples to monitor for $^{14}C$ carry-over. Water vapor degassing between preparations helped to remove residual $^{14}C$ remaining in the instrumentation. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (4,5). ANU sucrose, with an activity 1.508 times the $^{14}C$ activity of 1950 carbon, was used as analytical standard for the measurements. Measurements are reported in units of Modern or as DNA adducts/$10^{12}$ nucleotides. Modern is defined as $5.9 \times 10^{10}$ 14C atoms/g carbon and is approximately equal to the natural abundance of $^{14}C$ present in contemporary (1950 A.D.) carbon (6). Determination of adduct levels is based on $^{14}C$ measurement of the TCDD-DNA adduct. [$^{14}C$]-TCDD binding was calculated by subtraction of the natural radiocarbon content from the measured $^{14}C$ content of the samples. Adduct frequencies were normalized based on the assumption that 1 $\mu g$ DNA=3240 pMol deoxyribonucleotides. The lowest level of TCDD DNA bonding was detected at the 100 $\mu g$/kg TCDD dose level and corresponded to measurement of 1 TCDD deoxyribonucleotide adduct per $10^{12}$ deoxyribonucleotides. This dose level is approximately equal to the TCDD L.D.$_{50}$ (murine L.D.$_{50}$=125 $\mu g$/kg) for this species demonstrating that TCDD does not bond to DNA below levels acutely toxic to the organism. DNA from all other dose levels contained only the natural abundance of $^{14}C$ (1 Modern). $^{14}C$ content at the highest TCDD dose level was 5000 times lower that that detected for an equivalent dose of $^{14}C$ from 2-amino3,8-dimethyl [2-$^{14}C$]imidazo[4,5-f] quinaxaline treated mice demonstrating the ability of this protocol to remove non-covalently bond $^{14}C$ from the samples.

References:

1. Gupta, R. C. (1984) *Proc. Natl. Acad. Sci.*, USA 81, 6943–6947.
2. Vogel, J. S., Nelson, D.E., and Southon, J. R. (1989) *Radiocarbon* 31, 145–149.
3. Vogel, J. S. Nelson, D. E., and Southon, J. R. (1987) *Radiocarbon* 29, 323–333.
4. Davis, J. C. (1989) *Nucl. Instrum. Methods* B40/41, 705–708.
5. Proctor, I.D. (1989) *Nucl. Instrum. Methods.* B40/41, 727–730.
6. Stuiver, M., and Polach, H. A. (1977) *Radiocarbon* 19, 355–363.

EXAMPLE 5

Production and Measurement of $^{14}C$-Depleted Methanotrophic Bacteria.

Growth of $^{14}C$-depleted bacteria was carried out to obtain a $^{14}C$-free biological host for low-dose toxicology studies *Methylosinus trichosporium* Ob3b was obtained from Dr. R. Taylor (LLNL) and grown as described by Park et al (1). Briefly, the bacteria were grown in a 5 bioreactor with continuous gas flow. Temperature was maintained at 30° C. at pH 6.8-7.2. The methane (petroleum-derived) flow rate was kept at 150-500 ml/hr. The flow rate for air containing 10% $CO_2$ was kept at 450-1500 ml/hr. Approximately 1 mg of bacteria (wet weight) was collected 7 days after infusion of methane and dried under vacuum. The bacterial sample was converted to elemental graphite and measured by combusted to $CO_2$ in sealed, evacuated tubes with CuO at 700° C. and reduced to filamentous graphite by hydrogen over a cobalt catalyst as described by Vogel et al. (2,3). $^{14}C$-free acrylamide was used to measure the processing background $^{14}C$ content. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (4,5). ANU sucrose, with an activity 1.508 times the $^{14}C$ activity of 1950 carbon, was used as analytical standard. The bacterial carbon contained $^{14}C$ at the same concentration as the acrylamide processing blank, and was two orders of magnitude lower than the normal $^{14}C$ content of living organisms at equilibrium with the present biosphere.

References:

1. Park, S., Hanna, L. M., Taylor, R. T., and Droge, M. W. *Biotechnology and Bioengineering* (submitted).
2. Vogel, J. S., Nelson, D. E., and Southon, J. R. (1989) *Radiocarbon* 31, 145–149.
3. Vogel, J. S., Nelson, D. E., and Southon, J. R. (1987) 29, 323–333.
4. Davis, J. C. (1989) *Nucl. Instrum. Methods* B40.41, 705–708.
5. Proctor, I. D. (1989) *Nucl. Instrum. Methods.* B40/41, 727–730.

Results and Implications: Initial measurements of biological samples from $^{14}C$ tracer studies and of samples prepared in laboratories where $^{14}C$ is routinely used resulted in instrument contamination. As a result, new protocols were devised involving careful handling of each sample, use of disposable labware, and isolation of samples from potential sources of gross contamination. In addition, we alternated analytical standards (ANU sugar) with each DNA sample to determine when and if contamination occurred, and water vapor was flushed through the graphitization apparatus between samples to remove any excess $^{14}C$ left from the previous sample. We also used $^{14}C$-free acrylamide samples to test for sample contamination of either the graphitization apparatus or the spectrometer. Actual measurements were made on DNA diluted with $^{14}C$-depleted carbon prior to analysis. In one case, an 18,000 Modern sample was measured directly, but no residual $^{14}C$ from this sample could be detected in any of the subsequent sample preparations and measurements (data not shown). DNA from animals given the 5 mg/kg body weight dose of MeIQx averaged a 46,000-fold enrichment in $^{14}C$ but actual measurements at this dose were below 53 Modern due to dilution of the DNA with $^{14}C$-depleted carbon. In no case did the $^{14}C$-enriched samples contaminate either the graphitizer station or the spectrometer, as determined from the lack of a statistical increase in the $^{14}C$ content of the ANU sugar or acrylamide standards.

Instrument performance was determined by accessing the variation in measurements on replicate treatments and multiple measurements on the same sample. The coefficient of variation in $^{14}C$ content and number of adducts among animals at each dose level was approximately 10% by AMS. The average within-sample coefficient of variation in $^{14}C$ content of these measurements was 2% based on multiple measurements of standard $^{14}C$-containing materials, and was 8% for multiple measurements made on separately prepared aliquots of the same DNA.

Figure 2:
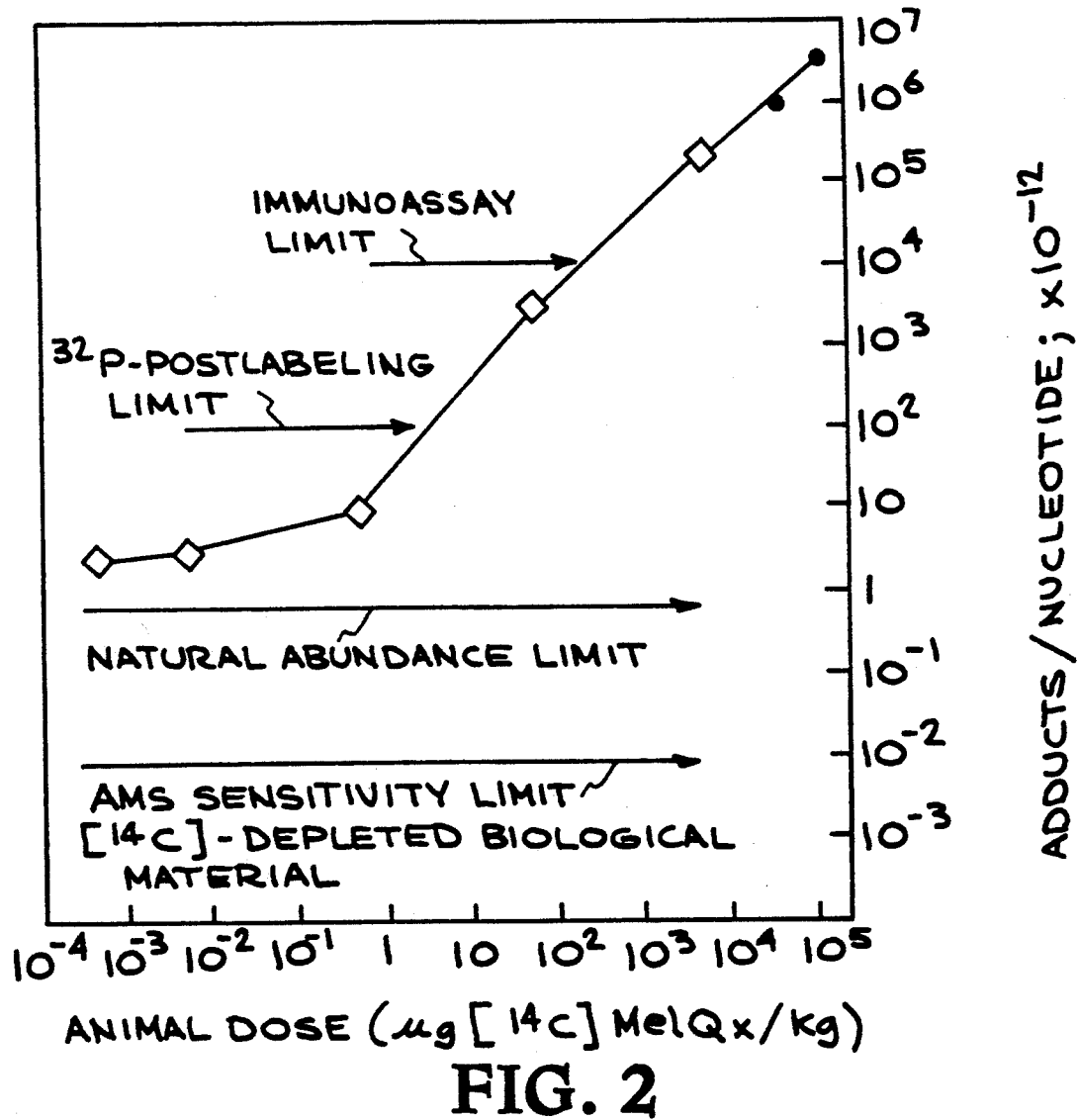
FIG. 2. Is a graph showing the effect of MeIQx exposure on DNA adduct levels found in the hepatic DNA of mice as determined by accelerator mass spectrometry ( ).

The amount of DNA analyzed in these experiments ranged from 1 $\mu g$ to 1 mg. Adduct levels per $10^{12}$ nucleotides were found to be dependent ($P<0.001$) on dose of MeIQx administered (FIG. 2). A linear relationship existed from a dose of 500 ng/kg of body weight to a MeIQx dose of 5 mg/kg ($P<0.001$). The $^{14}C$ content of the DNA of animals at eh 5 ng/kg dose are not significantly elevated (P<0.10) over levels detected in unexposed animals.

Figure 3:
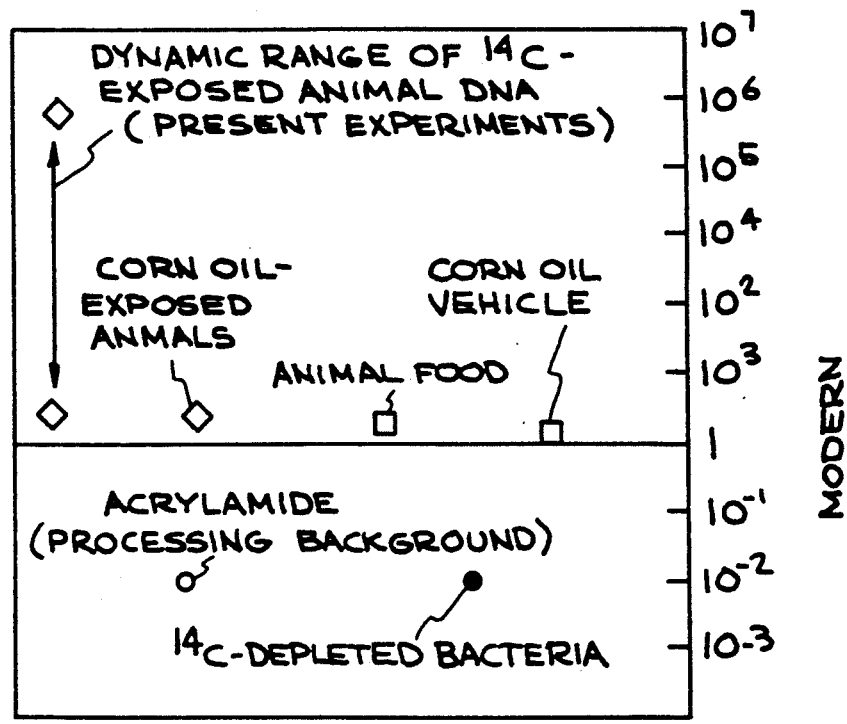
FIG. 3. Is a graph showing the $^{14}C$ content of control materials reported as fraction Modern (□, □, o) in relation to the range in values obtained for the [$^{14}C$] MeIQx-exposed mice ( ).

The measured $^{14}C$ content of the DNA from control animals, animal food, and other potential sources of $^{14}C$ utilized in this study are shown in FIG. 3 in relation to the $^{14}C$ content of the dosed animals. Animal food was found to be contemporary (1.2 Modern) as was the corn oil (1.15 Modern) used to administer the MeIQx. Samples prepared from $^{14}C$-free acrylamide consistently measured 0.01 Modern. Solvents and solutions used in the study were <0.01 Modern in $^{14}C$ content, but radiocarbon levels in surface swipes of work areas showed that some areas were contaminated with $^{14}C$ from previous tracer experiments. These areas ranged between 18 and 18,000 Modern (data not shown).

Figure 4:
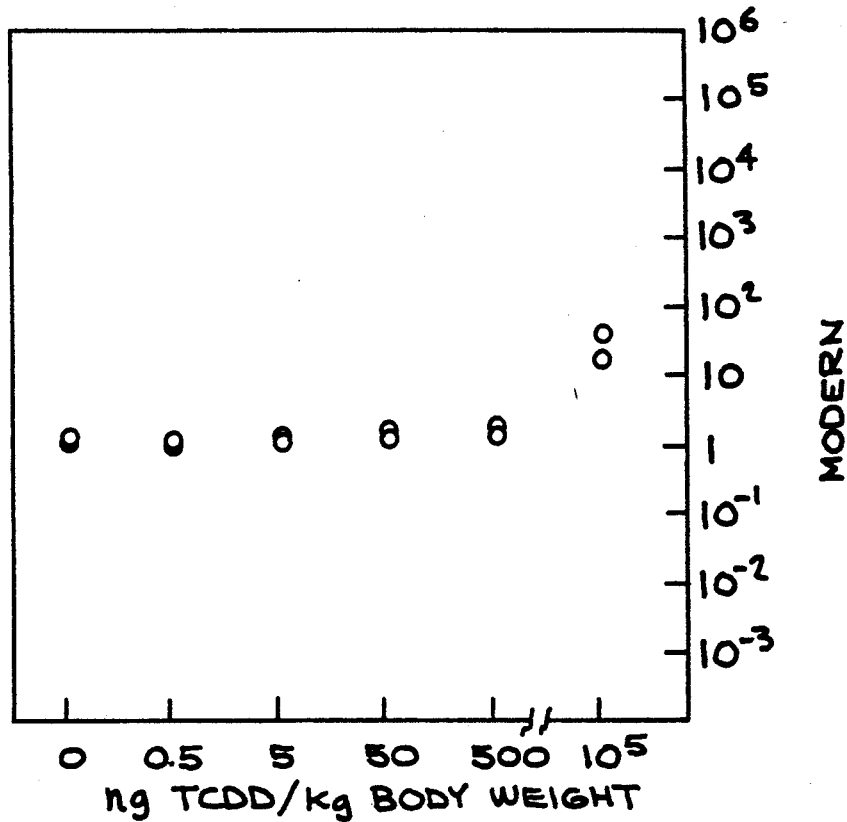
FIG. 4. Is a graph showing $^{14}C$ levels found in the DNA of [U-$^{14}C$]TCDD-exposed mice.

The extreme sensitivity of AMS for $^{14}C$ suggests that very small amounts of non-covalently bound $^{14}C$, or $^{14}C$-bound macromolecular contaminants in the DNA would be detectable, and thus could bias the adduct determinations. To evaluate this possibility and to ensure that our procedures adequately purify DNA, we measured DNA adduct formation with TCDD, a carcinogen which has not been found to covalently bind to DNA. TCDD absorption is rapid and approximately 33% of the administered dose should reach the liver tissue within the time frame of this study. These distribution kinetics are similar to that expected for MeIQx. The TCDD was uniformly labeled with $^{14}C$ (11.7 $^{14}Cs$ per molecule on average) corresponding to 10 times more $^{14}C$ at each dose level than the MeIQx-exposed animals. Hepatic DNA samples isolated from the TCDD-exposed mice (FIG. 4) were modern in $^{14}C$ content (1.06-1.7 Modern) except at the highest TCDD dose level (100 µg/kg; >14 Modern). The highest TCDD dose level is approximately the LD$_{50}$ for TCDD in mice and the significance of the higher [$^{14}C$]DNA values needs to be explored further. This data suggests that no (or little) nonDNA-bound $^{14}C$ remains after our DNA purifications since all DNA samples, except those from the highest TCDD dose, were modern in $^{14}C$ content. This suggestion is supported by the fact that $^{14}C$ levels measured in DNA from the MeIQx-exposed mice ranged from 100 to 4000-fold greater than with the TCDD-exposed mice. Even at the highest TCDD dose, greater than 99.9% of the $^{14}C$ distributed to the liver was removed through our DNA purification protocol. Additionally, this result shows that animal handling and DNA isolations can be carried out without radiocarbon contamination when done using appropriate procedures.

The limiting factor for biological measurements in the detection of [$^{14}C$]-tagged molecules will be the natural abundance of $^{14}C$ existing in the biosphere. Thus, we felt utilization of [$^{14}C$]-depleted hosts would be valuable for modeling dosimetry. Towards this end, *Methylosinus trichosporium* was grown using petroleum-derived methane as the sole carbon source. Measurement of the $^{14}C$ content of this organism verified that the $^{14}C$ content can be easily depleted to an equivalent of 0.01 Modern which is 200 times less than our lowest mouse sample (FIG. 3).

The present detection limit for [$^{14}C$]-labeled DNA adducts by AMS is 1 adduct/10$^{11}$ nucleotides. This corresponds to a one order of magnitude improvement over the very best sensitivity offered to date by the $^{32}P$-postlabeling assay. AMS provides a direct measure of the number of adducts present without relying on enzymatic recognition of adducts and/or quantitative extraction recoveries. In addition, these measurements are 3 to 5 orders of magnitude better than other techniques used for quantitative assay of DNA adducts such as ultrasensitive radioimmunoassays, surface enhanced Raman spectroscopy, gas chromatography mass spectrometry, laser-induced phosphorescence, fluorescence spectrometry, fluorescence line narrowing spectrometry, and synchronous scanning fluorescence spectrometry. Reproducibility of the measurements is very high (within 10%) and is limited by animal to animal variation.

Instrument precision in these measurements is 2% with further improvements likely. Thus AMS is a uniquely sensitive, and reproducible technique for adduct measurement and will easily complement existing methods.

The inability to measure adducts in animals given 5 ng MeIQx/kg and less is seemingly due to contamination of the DNA during isolation and does not represent a biological threshold. It is not the result of our inability to detect modern, or lower levels of $^{14}C$. Contamination most likely occurred during animal handling and/or DNA isolation. This is evident from comparison of the expected amount of $^{14}C$ in contemporary materials to the amounts actually found in the control animals (FIG.3). Measurement of corn oil and animal food corresponded to contemporary carbon (approximately 1.2 Modern) but control animals were 2-fold above contemporary in $^{14}C$ content. Measurement of acrylamide, and the $^{14}C$-depleted methanotrophic bacteria demonstrate the sensitivity of the carbon preparation and measurement process and that we can measure up to 100-fold below contemporary levels of $^{14}C$. Thus, the relatively high levels of $^{14}C$ found in animals not given radioisotope are due to sample contamination, and to the proximity of the total $^{14}C$ content of the samples to the ambient $^{14}C$ content of the DNA itself. Extreme care must be taken to avoid excess contamination above this natural limit. The work station that measured a minimum of 18,000 Modern aptly demonstrates the problems encountered in preparing samples for AMS measurement in laboratories with a history of $^{14}C$ use. However, the data from the TCDD exposure study shows that with proper procedures, contamination problems and non-specific binding of $^{14}C$ can be eliminated.

Additional increases of 2 to 10-fold in the sensitivity of DNA adduct detection by AMS will be possible through contamination reduction, but will certainly be no better than that allowed by the natural abundance of $^{14}C$ in biological molecules (modern carbon from the biosphere is 1/10$^{12}$ $^{14}C$). However, enhancement of sensitivity can be gained using $^{14}C$-depleted hosts. Growth of yeast and bacteria on petroleum feedstocks has been reported previously. We have grown $^{14}C$-depleted *Methylosinus trichosporiu* on petroleum derived methane and verified that the $^{14}C$ content can be easily depleted to an equivalent of 0.01 Modern, demonstrating a potential 100-fold increase in sensitivity. Such model organisms could be of use in studying the consequences of dose on the metabolism, kinetics, and effects of xenobiotic exposures. Growth of other hosts on petroleum based foodstuffs should result in similarly low radiocarbon backgrounds.

Clinical applications and research using human subjects can be envisioned with AMS radioisotope tracing. The detection sensitivity and small sample size requirements of AMS make it ideal for measurements of small quantities of easily accessible human cells, in addition to the liver tissue demonstrated here. Therapeutic parameters for individuals could be determined by AMS through administration of small dosages of $^{14}$C-labeled pharmaceuticals. Such custom tailoring of effective therapeutic regimens would be particularly valuable for cancer chemotherapy as the extremely small human radiation dose from the drug would not be an issue. The estimated effective [$^{14}$C]-MeIQx radiation dose equivalent in this study, based on a 24 hr biological half-life, corresponded to 0.003 milliSieverts at the 500 ng/kg dose level. This exposure is approximately 0.1% of the total annual adult exposure to ionizing radiation from known natural sources. Mutagen exposure, in such protocols, becomes a more significant issue than the radiation dose incurred.

Use of AMS in the present measurements of low-level DNA adducts provides no structural information on adduct type. Such information is better obtained with the postlabeling assay. However, molecular information on adduct type should be obtainable with AMS when it is used in conjunction with appropriate techniques to purify and separate adducts prior to measuring the $^{14}$C ratios. The need for use of radiolabeled compounds with AMS is a limitation, but radiation exposure, due to the extreme sensitivity of the technique, is insignificant, particularly when used in the laboratory and clinical setting where very low levels of isotopically-tagged compounds are being measured. AMS also has the advantage of measuring these low $^{14}$C levels in small samples. Utilization of rare stable isotopes seems possible as well. Thus AMS will be useful in any application where sensitivity of detection is limiting.

The present results with DNA adduct dosimetry demonstrate the utility of AMS for quantitive measurement of low-frequency biomolecular events following exposure to small concentrations of $^{14}$C-labeled xenobiotics. The technique will be useful in clinical and laboratory environments where sensitivity of detection is not possible by other assays and in a wide number of applications beyond the adduct detection reported here. The technique has a dynamic range covering many orders of magnitude, is reproducible, sensitive, and $^{14}$C contamination is controllable. Furthermore, requirements for $^{14}$C enrichment are 5-6 orders of magnitude below traditional decay counting methods. Other obvious candidate isotopes for low-level biomedical and environmental dosimetry applications are $^3$H and $^{41}$Ca. These potential new applications, coupled with the $^{14}$C measurements reported here, show AMS technology to be an important new tool for the biomedical and environmental sciences community.

EXAMPLE 6

RIA Detection of Heptachlor

Fifteen microliters of methanol containing 175 femtoMoles (65 picograms) of 8.3% $^{14}$C-labeled heptachlor is pipetted into a 0.5 milliliter, capped plastic centrifuge vial. Unlabeled heptachlor which is diluted in 5 microliters of methanol is also pipetted into the vial in either a known amount (when making a calibration curve) or an unknown amount (when assaying a sample). To this, we add 80 microliters of a 0.01 milliMolar solution of PBS (phosphate buffered solution) with 0.05% TWEEN 20 detergent and containing 67 femtoMoles (approximately 10 nanograms) of an antibody specific to halogenated hydrocarbons such as heptachlor. The solution is allowed to incubate overnight at room temperature with no agitation. Agitation is not required because all interactions between the antibody and the heptachlor take place in solution.

In this method, the antibodies along with their bound heptachlor, are separated from the unbound fraction of heptachlor by the addition of protein-coated glass beads to which the antibodies attach, such as are commercially available for use in affinity chromatography. The beads may be of some other material which does not cause non-specific binding of the heptachlor through hydrophobic reaction, as do acrylic beads or agarose beads in their various forms. The protein can be any one of the class of proteins which can be immobilised on the bead substrate and which bind to the constant heavy fraction of antibodies, such as the commonly used protein A or protein G. The amount of such protein is chosen to fully extract all of the antibodies but is also chosen to minimize the amount of labeled heptachlor which binds directly to the protein or bead substrate. For example, 10 microliters of a 0.05% (by volume) PBS solution of protein G on 150 micron diameter macroporous glass beads is added to the heptachlor/antibody vial. The vial is agitated for 1-2 hours to permit the binding of the protein and the antibodies throughout the volume. The vial is then centrifuged to separate the solution from the antibodies attached to the heavy glass beads. The remaining liquid is then pipetted or decanted away. The beads holding the antibodies are rinsed 5 times using 20% methanol and Tweenwith a centrifugal separation of the solvent and the beads each time. Finally, carbon carrier is added to the beads as 100 microliters of a solution containing 100 micrograms or more of a $^{14}$C-free detergent such as cetyl pyridinium chloride. The beads are pipetted from the reaction vial to a glass combustion tube using this detergent solution. In this method, this last pipetting of the bound antibodies on the glass beads to a clean, new combustion tube prevents the label heptachlor which is attached to the reaction vial from being counted in the final AMS analysis. The sample is combusted and measured as outlined in the following procedures.

In this method of determining heptachlor by RIA, 100 femtograms of unlabeled heptachlor is assayed as 7200 counts in the AMS detector, while the non-specific background from the beads is nearly 10,000 times lower. The cetyl pyridinium chloride is 1.6% Modern, in terms of its radiocarbon content, and introduces a constant offset in the final counted activity of 6% of the expected signal. Greater sensitivity is gained by using a radioligand which is labeled by one radiocarbon on each molecule. Further sensitivity is possible by using uniformly labeled radio-ligands such as p-TetraChloro-DibenzoDioxin (TCDD) in which each molecule contains, on average, 11.6 radiocarbon atoms. Thus, a sensitivity of 1 femtoMole of competitor TCDD is detectable using this method.

EXAMPLE 7

Sample Preparation Procedure

1. Adjusting sample size

AMS measurement of isotope ratios requires 100-2000 micrograms of material in the final physical form presented in the ion source. For example, carbon is introduced into the ion source as graphite, preferably on or with an iron, cobalt or other metal binder; chlorine is introduced as silver chloride; calcium is introduced as calcium hydride or fluoride, and hydrogen is introduced as titanium hydride.

The separated or purified biomedical samples are first adjusted for the amount of carbon or other element acting as the carrier for the tracer isotope(s). This is done by the addition of a known amount of the carrier, preferably in solution. This carrier is introduced at the earliest portion of the biomedical purification in a form which will survive the final purification procedures along with the extracted or purified samples containing the tracer to be quantified.

If the samples containing the tracer are much smaller than this added carrier, 1 microgram or less, for example, the absolute amount of the isotopic tracer in the original sample is found through multiplying the measured isotope ratio by this known amount of tracer-free carrier. This is the case, for example, in the measurements of small amounts of purified DNA in order to determine the number of genotoxic or chemotherapeutic molecules which have adhered to the DNA. Another example of this absolute tracer determination through dilution in carrier is the measurement of the tracer content of competitive radio-immunoassays, in which less than a microgram of material will be diluted into a larger carrier sample. In the case of $14_C$ detection, these carriers are chosen to be as free of $14_C$ as possible. Compounds used for this application must be produced substantially from fossil carbon, derived from petrochemicals or coal. One class of compounds which has useful properties in this regard is the ionic biological detergents, such as cetyl pyridinium chloride or benzalkonium chloride. The detergents must be tested for $14_C$ content before use, however, since some of them are produced using varying amounts of compounds derived from plants or animals, which contain $14_C$ in concentrations similar to the present atmospheric concentration. Sodium dodecal sulfate (SDS), a common detergent used in mobilizing proteins, is one such detergent derived from plant matter. The exact detergent or other carrier is chosen to mix well with the final purified form of the biomedical sample.

Large samples of animal or plant tissues, excreta, or fluids contain enough of the element to be assayed and do not need to be diluted before preparation of the proper physical form for introduction into the ion source. For example, the determination of the pharmacokinetics of a chemotherapeutic or other agent can be determined by radio-isotopic labeling of the agent before administration. The presence of the agent can then be determined in any tissue or fluid by detecting the ratio of the radio-isotope directly in that tissue or fluid, if 100–2000 micrograms of the tissue or fluid is available. This constitues several milliliters or less of blood or urine, or several milligrams of tissue. In order to determine the absolute amount of the agent in the tissue or fluid, however, the concentration of the assayed element in the original tissue or fluid must be known. In the case of carbon or hydrogen, this is accomplished through the separate combustion of another aliquot of the material and quantification of resultant gases, through the use of an ordinary carbon-nitrogen-hydrogen analyzer, for example. Dilution of samples such as these tissues or fluids may still be required to avoid the introduction of excessive amounts of the radio-isotope into the ion source. For example, carbon samples that contain $14_C$ at concentrations over 100 times that found in the present atmosphere strain the detection system, and samples over 10,000 times that level contaminate the ion source for a short period of time. In these cases, carefully quantified amounts of the sampled tissue or fluid and a $14_C$-free carrier such as a petrochemical, coal, or charcoal produced from >40,000 year old tree must be combined before proceeding to further preparation.

Samples which contain 1–100 micrograms of the element to be assayed for radio-isotopes must be enlargened to amounts which can be further processed. Since the ratio of the radio-isotope to the stable isotope of the element will depend on the ratio of the sample to the added carrier, both must be carefully quantified as discussed in the above paragraph.

2. Production of a uniform material

The biomedical sample, with or without an added carrier compound, is comprised of different molecules, and the radio-isotopes to be quantified may be bound in different parts of these molecules. It is these differing possible states of the bound radio-isotopes which can often cause mis-quantification of the isotope content through traditional biomedical scintillation counting. Precipitation of parts of the sample and quenching interactions with the scintillant are two such possible problems. In AMS measurements, molecular information is lost in the interest of complete, efficient counting of the radio-isotope. For this purpose, the element of interest is completely separated form all other elements in a sample.

For example, chlorine or calcium can be precipitated in various forms from solution after the sample has been thoroughly hydrolyzed in strong acids. In the case of carbon or hydrogen, this uniform elemental extraction is most easily accomplished through the thorough combustion of the sample. The resultant carbon dioxide or water can be cryogenically separated from other combustion products.

For example, the samples for $14_C$ analysis are adjusted for size and isotope content as discussed above. They are placed in 6×50 mm disposable culture tubes, which have first been heated in an oven in air to 500° C. in order to combust any residual carbon on their surfaces. The tubes are then handled using precautions to avoid fingerprints or other surface contamination. Use of dry latex gloves or forceps are examples of such precautions. The samples are completely dried through lyophilization or vacuum centrifugation in these tubes. A solid oxidant, such as wire-formed cupric oxide, is added to the culture tube containing the dried sample. Approximately 0.5 grams of cupric oxide to a milligram of sample is sufficient to insure complete oxidation of the sample. The culture tube containing the sample and the oxidant are placed into a 9×150 mm quartz, closed-ended, combustion tube. Prior to use, these quartz tubes are heated to 900° C. in air in order to remove any surface carbon. They are stored in a sealed enclosure which is open to a container of water which had been made basic with sodium hydroxide. The large tube is then evacuated and sealed at a length of approximately 100 mm using an an oxyacetylene torch. A number of the sealed, evacuated tubes containing the samples and the oxidant are placed in an array of ceramic tubes. This array of ceramic tubes is one means of keeping the combustion tubes in order so as not to confuse the samples, and it prevents the occasional over-pressuring of one tube from damaging the other tubes. The tubes are heated to 650° C. in a muffle furnace for 1½ hours to complete the combustion, after which they are slowly cooled. Alternatively, combustion may be accomplished in a stream of oxygen at high temperatures. The resultant carbon dioxide or water are purified from the other combustion products through cryogenic separation.

Figure 6:
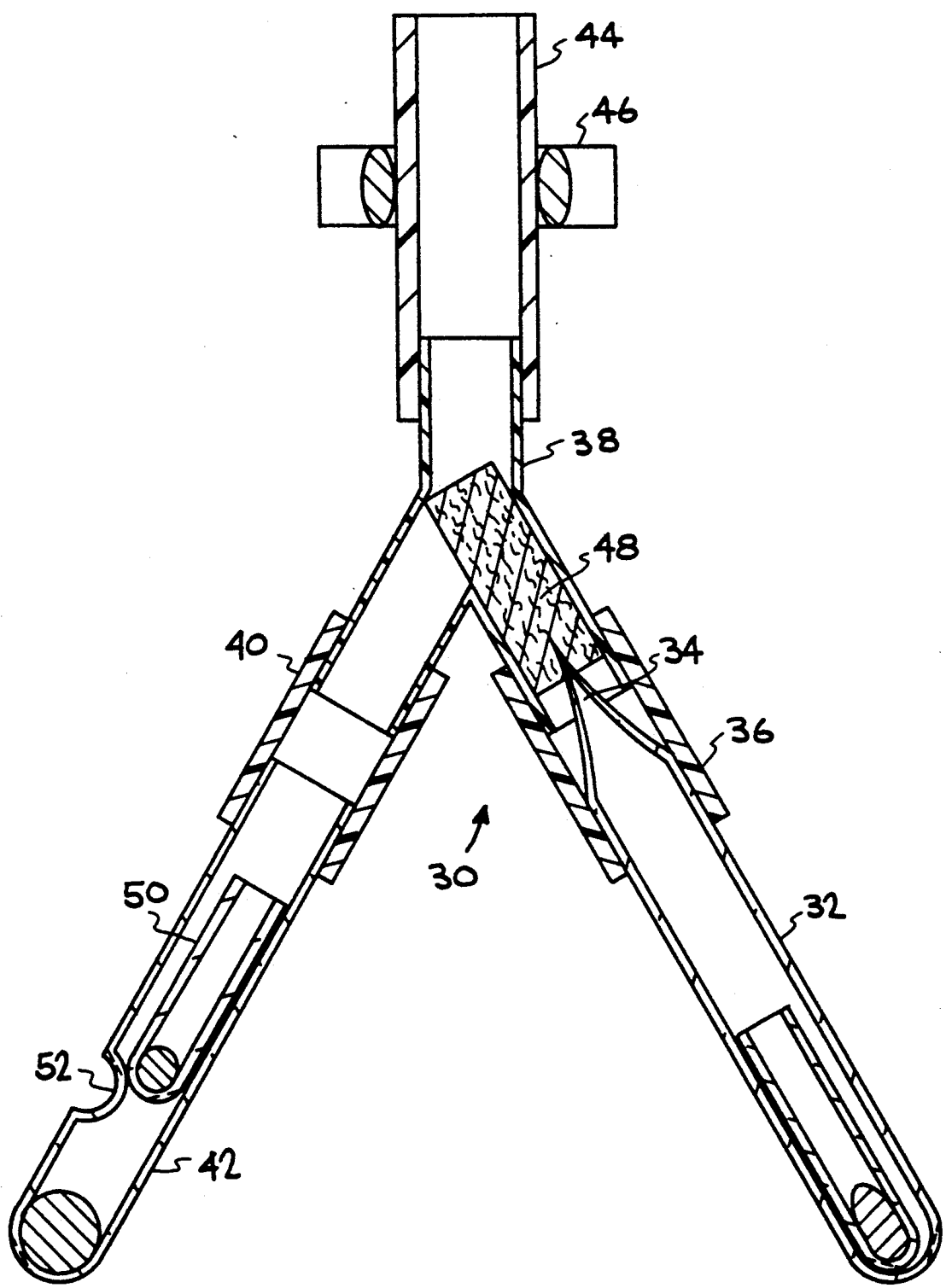
FIG. 6. Is a schematic drawing of specific apparatus used in conducting a radio-immune assay.

The cryogenic separation of the desired combustion products is done in a manner to avoid cross contamination of samples, which can occur through gas adsorption/desorbtion on the walls of a common manifold. In this method, a disposable transfer manifold 30 is used for each sample, as shown in FIG. 6. The quartz combustion tubes 32 are produced so that the initial closed end comes to a thin, breakable point 34. This point is inserted into a short length of flexible plastic tubing 36, which is connected to one short arm of an inverted, hard plastic 'Y' 38. The other short arm of the inverted 'Y' 38 is connected through a similar short length of flexible plastic tube 40 to a closed-end, borosilicate glass tube 42 which contains metal catalysts and reactants as described in the next section. The long arm of the plastic 'Y' 38 is connected via a slightly longer piece 44 of flexible tubing to an evacuation manifold (not shown). The assembly is evacuated. The combustion tube 32 is immersed in a dewar containing a dry ice/alcohol slush in order to retain the water resulting from the combustion of the sample in the combustion tube. The other glass tube 42 is immersed in liquid nitrogen. After evacuation, a hose clamp 46 closes the plastic assembly 30 from the evacuation port. The weak point 34 of the combustion tube 32 is then broken by pressing it against the inside of the hard plastic 'Y' 38 which also contains a plug of glass wool 48. The released carbon dioxide is frozen into the borosilicate glass tube 42. After sufficient time to allow maximal condensation of the carbon dioxide, the hose clamp 46 is removed and the nitrogen gas from the combustion of the sample is pumped away. The borosilicate glass tube 42 is then sealed using a torch. The sealed tube is then allowed to warm with the carbon dioxide trapped within it.

If the hydrogen from the same combustion is to be analyzed for tritium, the hydrogen from the same sample is then recovered as water vapor in a tube containing the appropriate metal reactants for the later reduction of the water. A second 'Y' is attached (by its long arm) to one short arm of the first 'Y' and the breakable tip of the combustion tube 32 is attached to the other short arm as described above. In this method, one short arm of the second 'Y' connects to the glass tube to which the carbon dioxide is condensed, and a second glass tube is connected to the other short arm in order to separate the water vapor. This is done by again sealing the plastic assembly from the evacuation port using a hose clamp after the tube containing the carbon dioxide has been sealed and removed. The dry-ice slush is then moved from the combustion tube to the remaining glass tube. As the combustion tube warms, the water will re-condense in the glass tube, which can be sealed in the same manner as the tube containing the carbon dioxide. Alternatively, the carbon dioxide can be evacuated directly if only the hydrogen traces is to be followed.

3. Transformation to a form suitable to the ion source

The uniform material, carbon dioxide, water, or acidic solution, containing the radio-isotope to be quantified is converted to a form suitable for use in an ion source. Ion sources using a gas as a sample material have been developed, as have ion sources which could directly break molecular bonds and ionize the individual elements. Such ion sources appear to have advantages in measuring large numbers of samples from biomedical or other survey studies. However, the work to which this method is to be applied necessarily results in consecutive samples which contain very different amounts of the isotope to be assayed. In some gas or other direct feed ion sources, the cross contamination between consecutive samples has been shown to be high, requiring long periods of time between sample measurements to allow the ion source to be cleansed through evacuation and/or heating. In this method, we use a fast-ion-bombardment sputter source of conventional form which uses a solid as the sputterable cathode material. An ion source using a non-volatile solid allows rapid, non-contaminating sequencing of samples. The conversion of the uniformly mixed material created in the previous step is made rapid and replicatable, so that the overall efficiency of measurement is not degraded in this chemical step.

For example, chlorine samples are precipitated as silver chloride from the digesting fluid of the previous step. Further purification must be done to reduce the interfering $^{36}S$ from the sample if $^{36}Cl$ is to be detectable. This is accomplished through several successive dissolutions and reprecipitations as silver chloride.

Both hydrogen and carbon are reduced to elemental form from the oxidised gases produced in the preceding combustion through reduction over zinc powder in the sealed tubes to which they have been separated. The resulting elemental hydrogen gas is absorbed into titanium. This titanium hydride comprises the material which is sputtered in the ion source. In this method, the titanium is contained in a smaller tube 50 within the mm sealed tube 42 of the previous step, while the zinc reductant is held in the bottom of the large tube. The small tube 50 is held off the bottom of the large tube 42 and away from the zinc powder by a dimple 52 which has been made in the large tube by heating a small area of the tube while the tube was evacuated. The sealed tube 42 is then heated to 400°–450° C. in an oven while the zinc reduces the water vapor. After several hours of such reduction, the tube is removed from the oven and the portion of the tube containing the titanium is heated to 550°–650° C. to absorb the hydrogen gas, either through a resistive tube heater or through direct radiofrequency heating of the titanium. Alternatively, the end of the sealed tube containing the zinc can be heated to 400°–450° C. by one heater while the end of the tube containing the titanium is heated to 550°–650° C. by another heater. Production and absorbtion of the hydrogen gas is done continuously.

Carbon dioxide is reduced to carbon monoxide within a sealed tube by zinc powder (as suggested by Slota, et al.) which, unlike their implementation, is placed in the bottom of the tube. This carbon monoxide is then reduced to filamentous graphite on an iron or cobalt catalyst, producing carbon dioxide which can be subsequently reduced again by the zinc. This reduction of carbon dioxide by zinc and iron-group metals is used by others, as is the more precise and complete reduction of carbon dioxide over iron-group metals by hydrogen (the 'Vogel'method). The present method differs from these other procedures by combining the reducing abilities of both hydrogen and zinc in a sealed tube to obtain a more rapid and complete reaction at a lower temperature than is used in the previous art. Zinc powder is placed into the bottom of the tube, and titanium hydride (20–40 mg $TiH_2$ per 1 mg of expected carbon) is added to the zinc powder. The iron or cobalt catalyst (1–10 mg to 1 mg of expected carbon), on which the elemental graphite forms, is held in a similar tube within the larger tube. This smaller tube is held away from the zinc and titanium hydride by a dimple in the larger tube. After sealing the carbon dioxide in the large tube as described above, the complete large tube is heated in an oven to 435° C. for 5 or more hours. Hydrogen gas is evolved from the titanium hydride at this temperature, and this hydrogen gas speeds the reduction of both the carbon dioxide and carbon monoxide on the metal catalyst. The zinc further reduces the resultant water vapor back to hydrogen. Reductions using this method are completed in 5 hours instead of the 12–24 hours required when zinc alone is used for reduction. This method has the further advantage of decreasing the amounts of zinc which migrate to the iron-group catalyst through intermediate volatile chemical forms, such as carbonyls. The presence of zinc and, particularly its oxide, in the final graphite on the iron-group catalyst decreases the efficiency of the final ion production in the ion source. Thus, this method of including both zinc and hydrogen in the reduction of carbon dioxide rapidly produces filamentous graphite with low isotopic fractionation and high ion current output.

This method of reduction and conversion to graphite at a single temperature has obvious benefit batch processing of large numbers of biomedical or other survey samples in a simple furnace. The number of reaction tubes which are processed is limited merely by the size of the oven, and the method of transferring the gases from combustion to the sealed reaction tubes requires only a few minutes per sample.

4. Presentation of the sample in the ion source

The solid produced in the previous step is stored in a manner to avoid possible contaminants until needed. In the case of chlorine purified as silver chloride, care is taken to prevent adsorption of sulfur from the air during storage and handling. Thus, the prepared samples are stored in tightly sealed containers and handled preferably within an inert-gas glove box. The solid materials to be assayed for carbon or hydrogen isotope content are left sealed within their reaction tubes until needed.

The solid sample to be assayed is pressed into an aluminum, or other suitable material planchet. In example of carbon or hydrogen, the sealed reaction tube 42 is scored and broken below the level of the smaller tube 50 containing the titanium hydride or the graphite on metal catalyst. The small tube 50 is then extracted from the reaction tube 42 closed end first. This direction or extraction minimizes the amount of tiny glass shards from the breaking operation which can mix with the solid sample. Such bits of glass are detrimental to the sputtering process in the ion source. The small tube is then tipped over the sample holder and the solid sample, usually in powder form, is vibrated out of the tube and into the well in the sample holder. A metal rod of the same diameter as the sample-containing hole is used to press the sample into the hole, using either a simple hammer or a pneumatic press. A new metal rod is used to press each sample, if the samples are expected to have isotope concentrations differing by more than factors of 1000. Alternatively, similar samples are pressed with the same rod, but only after the end and side surfaces of the rod have been cleaned through abrasion.

The loading of the sample material into the planchet is done as close to the time of measuring as is possible, in order to minimize contamination of the sample through adsorption. Alternatively, a number of the samples are pressed into holders and stored in inert atmospheres until use.

5. Measurement of the isotopic ratio

The planchet containing the sample is loaded into the multi-sample ion source wheel along with others of the same experimental set and along with a suitable number of samples containing known amounts of the isotope to be assayed ("standards" and "secondary standards"). The sample is sputtered to produce negative ions, and theses ions are extracted by high voltages, analyzed magnetically and electrostatically before being injected into a tandem accelerator mass spectrometer. This injection process sends the isotopes of interest into the accelerator sequentially, under computer control, or simultaneously. The accelerator mass spectrometer separates the accelerated ions by mass, velocity, charge and energy. The ratio of the rare to common isotopes in the sample is determined according to existing art. For example, the rare isotope is counted as individual particles by any of a number of common detectors, such as gas ionization detectors or silicon solid-state detectors. The stable or common isotope produces an ion beam from the accelerator which is sufficiently intense to be measured in a current-detecting Faraday cup coupled to a charge-integrating circuit. A comparison of the number of rare isotopes to one or more of the common isotopes of that element is derived from these measures of the number of detected rare isotopes to the amount of detected common ion current.

A similar ratio for standard samples are determined, and a comparison of the two ratios allows the determination of the amount of the rare isotope in the unknown sample relative to the known amount in the standard sample. This comparison is only valid if the standard samples are treated and prepared in a manner analogous to the preparation of the biomedical sample.

In the prior art of AMS, the rare isotope is detected up to levels of 1000 times the detection sensitivity. In this method, biomedical samples may contain the rare isotope in concentrations of one million or more above the detector sensitivity. Thus, simpler, single ionization detectors can be used as alternatives to the usual multi-anode, isotope-identifying, ionization detectors. In this method, the simple count rate of the detector in the energy range of the isotope to be detected is compared directly to the ion current of the common isotope.

6. Quantification of the radio-isotope concentration in the original sample

AMS detects the concentration of radio-isotopes with respect to one or more of the stable isotopes of the same element. In biomedical applications, the data is more useful as the concentration of the rare isotope with respect to the mass of the initial sample or the absolute number of the rare isotopes. This quantification requires a measure of the stable isotopes in the original sample, so that an isotope ratio can be converted to a concentration of the rare isotope to the mass of the sample.

In the case of a very small sample (less than 1 microgram, for example) which is diluted with a comparatively large amount (>100 micrograms, for example) of carrier as described above, the concentration of the rare isotope in the original sample is found by merely multiplying the measured isotope ratio times the known amount of the stable isotope added as carrier. An aliquot of the carrier substance must also be processed and measured in complete analogy to the samples, in order to determine the concentration of the rare isotope which is added to the sample by the carrier and subsequent preparation procedures. This measure of the absolute amount of rare isotope in the sample is used directly, to compare amounts of that isotope in sequential assays which produce the same size sample for differing amounts of initial reactants. Quantification of the bound amount of radio-isotope in a radio-immune assay is just one such example. Quantification of isotope-labeled chemical adducts on small fractions of DNA is another example. Other elements, such as selenium, which have low natural concentrations in biological samples are quantified by this addition of a comparatively large amount of elemental carrier.

When the biomedical sample is sufficently large to be measured directly in AMS (>50 micrograms, for example) The isotope ratio determined by AMS is converted to a concentration of that isotope per mass of the sample by multiplying the isotope ratio by the concentration of the stable form of that element contained in the sample. This concentration is obtained by weighing the sample carefully before preparation and then determining the amount of the purified element of interest which results from the preparation procedures outlined above. Alternatively, a different analysis technique is used to determine the amount of the stable isotopes in a separate, known amount of the sample. For example, a tissue is assayed by AMS for radiocarbon content as an indicator of a labeled compound remaining in the tissue. The result is a radiocarbon concentration per total carbon content. The carbon content of the tissue is determined by combustion of a carefully weighed separate aliquot of the tissue to produce carbon dioxide. The amount of this carbon dioxide is measured either manometrically or chromatographically, as is done by commerically available carbon, nitrogen, hydrogen and sulfur analyzers.

A carrier is also added to the biomedical sample if the sample is too small (1–50 micrograms, for example) for direct AMS measurement, but is too large for the stable isotope concentration to be dominated by a reasonable amount of known carrier. In this case, detailed mass balance of the rare and stable isotope content of both the sample and the carrier is required to obtain the concentration of the rare isotope in the original sample.

EXAMPLE 8

A simulation of the sensitivity to be expected in an AMS based RIA was performed using the standard equations relating bound fraction of radio-labeled TCDD(dioxin) to the concentrations of non-labeled dioxin. The binding antibody is assumed to be attached to small, suspendible glass spheres which allowed free exchange throughout the solution. Separation of the bound antibody-ligand fraction from the solution containing the unbound radio-ligand is effected by centrifugation, followed by rinsing and further centrigation. The separated beads holding the antibodies and the bound radio- and natural ligands are mixed with several hundred μg of radiocarbon-free carbon, such as can be introduced in the form of certain ionic detergents. The samples are prepared for measurement by accelerator mass spectrometry, either through combustion to carbon dioxide and subsequent catalytic conversion to filamentous graphite, or through modification in molten Lewis acids. The radioisotope measurement are made using the usual practice of accelerator mass spectrometry. Femtomole sensitivity is found for 100 μl solutions containing 0.5 picomole of the antibody and 0.25 picomole of the uniformly C-14 labeled competitive dioxin ligand. The dissociation constant, required for a realistic simulation, was assumed to be similar to that measured by an immunoassay performed by Bradfield and Polant (Mol. Pharm. v. 34, pp.682–688, 1988), who used a label of iodine-125 to replace a chlorine in the dioxin molecule.

The foregoing description of preferred embodiments of the invention have been presented for purposes of illustration and description. It is not intended to be exhaustive or to limit the invention to the precise forms disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto and their equivalents.

We claim:

1. A method of quantifying molecules in biological substances, comprising:
   a. selecting a biological host comprising biological substances in which radioisotopes are present in concentrations equal to or less than the concentration in the ambient biosphere,
   b. preparing a radioisotope-labeled reactive chemical specie,
   c. administering said chemical specie to said biological host in doses sufficiently low to avoid significant damage to the host's biological system,
   d. allowing a period of time to elapse sufficient for dissemination and reaction of said chemical specie with said host throughout said biological system of said host,
   e. isolating a reacted fraction of a sample of biological substance from said host in a manner sufficient to avoid contamination of the fraction from extraneous sources of the radioisotope,
   f. converting said fraction of biological substance to a product material which efficiently produces charged ions in an ion source without introduction of significant isotopic fractionation, and
   g. measuring the radioisotope concentration in the product material using an accelerator mass spectrometer.

2. The method of claim 1, wherein said reactive chemical specie of step (b) comprises exogenous carcinogens, mutagens, teratogens or other chemicals labeled with a long-lived isotope selected from the group consisting of $^3$H, $^{14}$C, $^{26}$Al, $^{36}$Cl, $^{41}$Ca, $^{79}$Se, and $^{129}$I.

3. The method of claim 1, wherein said chemical specie is covalently bound in step (d) to at least one of the nucleic acids, nucleotides, or nucleoside precursors in said biological host.

4. The method of claim 1, wherein the reacted fraction of step (f) contains host nucleic acids, and step (g) comprises measuring the radioisotope concentration in said host nucleic acids.

5. The method of claim 1, wherein said chemical specie of (b) comprises chemicals of unknown affinity for covalent binding to nucleic acids, the product material of step (e) comprises nucleic acids covalently bound to said chemical specie, and step (g) comprises measuring the radioisotope concentration of said nucleic acids.

6. The method of claim 1, wherein said biological host of (a) is a mouse, said reactive chemical specie of (b) comprises aminoimidazoazaarenes labeled with $^{14}C$ at non-labile molecular positions, said fraction of (e) comprise hepatic tissue of mice, and step (g) comprises measuring the radioisotopic concentration in the DNA of the hepatic tissue.

7. The method claim 2, wherein said reactive chemical specie of (b) interacts with intermediary proteins or peptides of said host, and step (e) is carried out be extracting and purifying reacted specie or reacted specie-protein complex.

8. The method of claim 7, wherein said biological host of (a) contains hepatic or other mammalian cells having 2,3,7,8-tetrachlorodibenzo-p-dioxin bound to the hydrocarbon receptors thereof, said chemical specie of (b) is 97% $^{14}C$-labeled 2,3,7,8-tetrachloro-dibenzo-p-dioxin, said fraction of (e) is isolated from at least one of cell membranes, cytosol, cell nuclei, or other cell components, and step (g) comprise measuring the radioisotope concentration in 2,3,7,8-tetrachloro-dibenzo-p-dioxin and its ligand receptor combination.

9. The method of claim 1, wherein said chemical specie of (b) comprises radioisotope-labeled natural or manufactured xenobiotics.

10. The method of claim 9, wherein said biological host of (a) is a mouse, wherein said chemical specie of (b) is phenyl-imidazo-pyridine and wherein said fraction of (e) is selected from the body and excreta of said mouse.

11. The method of claim 2, wherein said chemical specie is a chemotherapeutic agent and wherein said fraction of (e) is chosen from the excreta, plasma, and biopsies of the affected areas and organs.

12. The method of claim 11, wherein said fraction of (e) is selected from an organ, tumor, plasma, group of exfoliated cells, nucleic acids or other portions of the biological host.

13. The method of claim 12, wherein the dosage of said chemotherapeutic agent to said host is adjusted or titrated according to the quantification of the agent reaching specific desired organs, tumors, or other parts of said host.

14. The method of claim 1, wherein said reactive chemical specie of (d) is a labeled ligand, said fraction of (e) comprises a receptor molecule or an antigen receptor molecule and antigen complex and step (g) comprises measuring the radioisotope concentration of labeled ligand in said receptor molecule of said antigen.

15. The method of claim 14, wherein the biological host of (a) or fraction thereof contains endogenous or exogenous chemicals disseminated therein, said reactive chemical specie of (b) is a radioisotope-labeled analogue of said chemical, and said fraction of (e) contains common binding receptors of said chemical and its labeled analogue.

16. The method of claim 14, wherein the amount of 2,3,7,8-tetrachloro-dibenzo-p-dioxin is measured by competitive binding against $^{14}C$-labeled 2,3,7,8-tetrachloro-dibenzo-p-dioxin on specifically prepared antibody receptors of the dioxin.

17. The method of claim 1, wherein said biological host of (a) or fraction thereof comprises a quantity of receptors, antibodies or other proteins which have been labeled with a second radioisotope, said relative chemical specie of (d) is a labeled ligand capable of reversible or covalent bonding with said labeled receptors, antibodies, or other proteins, and wherein said biological host of (a), and said reactive chemical specie of (b), have been labeled in a manner such that the two radioisotope labels can be separately measured, either through their different identity or through specific extraction, isolation, and purification of the ligand from the receptor, antibody, or the other protein.

18. The method of claim 17, wherein said biological host of (a) comprises a receiving antibody labeled with a second radioisotope, and said reactive chemical specie of (b) is a competitive ligand labeled with a different radioisotope than said biological host, said fraction of (e) comprises a bound combination of said labeled biological host and said reactive chemical specie, and wherein step (g) comprises the specific measurement of the individual radioisotope of said labeled biological host, and said reactive chemical specie.

19. The method of claim 18, wherein said labeled biological host is labeled with a radioisotope selected from the group consisting of $^3H$, $^{14}C$, $^{79}Se$, and $^{129}I$, and said chemical specie is labeled with a radioisotope selected from the group consisting of $^3H$, $^{14}C$, and $^{36}Cl$.

20. The method of claim 1, wherein said reactive chemical specie comprises a multiple isotopic labeled exogenous substance, and step (e) comprises the isolation from a single biological system of said multiple isotopic labels.

21. The method of claims 17, 18, 19 or 20 wherein said multiple isotopic labels and said isotopes are detected from a single sample material in the ion source of step (f), said ion source being an accelerator mass spectrometer facility which injects the different ions into an accelerator system alternately.

22. The method of claims 17, 18, 19, or 20 wherein said multiple isotopic labels and said isotopes are detected from a single sample material in the ion source of step (f), said ion source being accelerator mass spectrometer facility which injects different ions into an accelerator system simultaneously.

23. The method of claims 17, 18, 19, or 20 wherein said fraction of biological substances isolated in step (e) has been specifically extracted, purified, and diluted and has been treated with strong Lewis acids, and wherein the isotopic labels of $^3H$, $^{14}C$ and the isotopes are detected from a single sample material in the ion source of step (f).

24. The method of claim 1, wherein said biological host of (a) has been grown on food or precursors which have been produced, manufactured, or grown from stocks which are depleted in the radioisotope to be used in biotic tracing.

25. The method of claim 24, wherein said biological host comprises methanotropic or other bacteria grown on methane and carbon dioxide derived from petroleum or natural gas whereby the bacteria are depleted in $^{14}C$, and the reacted fraction can be detected within these bacteria at $^{14}C$ concentrations below the $^{14}C$ concentration of the present day natural biosphere.

26. The method of claim 24, wherein said biological host of (a) comprises terrestrial or aquatic plants grown on materials depleted in the radioisotope to be used in biotic tracing.

27. The method of claim 26, wherein said terrestrial or aquatic plants are grown on petroleum or coal-derived $CO_2$ which is depleted in $^{14}C$.

28. The method of claim 24, wherein said biological host comprises terrestrial animals or aquatic biota grown on food produced from yeast, bacteria, plants, or other organisms whose constituents have been derived primary from stocks depleted in the radioisotope to be used in biotic tracing.

29. The method of claim 28, wherein said biological host of (a) comprises several generations of mice or other small animals grown on food produced from yeast, bacteria, or other organisms whose constituents have been derived primarily from petroleum or natural gas depleted in $^{14}C$ to be used in tracing exogenous chemical including nutrients, which are labeled with $^{14}C$ at concentrations greater than or equal to the $^{14}C$ concentration of the present day natural biosphere.

* * * * *